United States Patent [19]

Shipp

[11] Patent Number: 5,374,813
[45] Date of Patent: Dec. 20, 1994

[54] SURGICAL INSTRUMENT RECYCLING AND TRACKING SYSTEM

[75] Inventor: John I. Shipp, Tullahoma, Tenn.
[73] Assignee: Life Surgery, Inc., Tullahoma, Tenn.
[21] Appl. No.: 962,489
[22] Filed: Oct. 15, 1992
[51] Int. Cl.$^5$ .............................................. G06F 15/42
[52] U.S. Cl. ..................................... 235/375; 235/385; 364/413.01
[58] Field of Search ................. 235/375, 385; 364/403, 364/413.01

[56] References Cited

U.S. PATENT DOCUMENTS

| | | | |
|---|---|---|---|
| 4,514,815 | 4/1985 | Anderson | 235/385 |
| 4,974,166 | 11/1990 | Maney et al. | 235/375 |
| 5,038,283 | 8/1991 | Caveney | 235/385 |

*Primary Examiner*—Davis L. Willis
*Assistant Examiner*—Peter J. Rashid
*Attorney, Agent, or Firm*—Mark J. Patterson; Edward D. Lanquist, Jr.; I. C. Waddey, Jr.

[57] ABSTRACT

A system for recycling and tracking of reusable surgical instruments includes a remotely located instrument sterilization and maintenance facility, electronically linked to a shipping carrier and a hospital facility. Orders for surgical instrument kits needed during a predetermined surgical schedule are placed electronically from the hospital site and transmitted to a host computer at the remote sterilization and maintenance facility. Instrument kits are stored at the sterilization and maintenance facility which also receives used instrument kits from the hospital. Decontamination, inspection, repair, recycling, and sterilization stations at the sterilization and maintenance facility allows for rapid, efficient, and low cost maintenance and repacking of used instruments for reuse at the hospital.

Bar code readers connected to remote data terminals located at the hospital, at the maintenance facility and on board the shipping carrier track electronically the inventory and location of instruments needed by the hospital.

7 Claims, 2 Drawing Sheets

SURGICAL INSTRUMENT RECYCLING AND TRACKING SYSTEM

BACKGROUND OF THE INVENTION

The present invention relates generally to the use, inventory tracking, and recycling of instruments used in surgical procedures.

Most hospitals perform numerous surgical procedures each day, requiring a complex and labor intensive system of instrument de, contamination, inspection, and sterilization. In addition, to accommodate the need for rapid turnover of operating rooms between procedures, a large inventory of instruments and related equipment must be maintained at the hospital so that procedures will not be delayed while waiting for clean and sterile instruments. Obviously, valuable floor and shelf space in the surgical suite must be dedicated to such inventory, as well as to equipment for the cleaning, inspection, and sterilization of the instruments.

Often, surgical instruments and related equipment are damaged or substantially degraded during use, necessitating repair before they can be used again. To achieve an adequate level of performance in the inspection and repair of such instruments, employees having a relatively high skill level are needed. Moreover, many reusable surgical instruments are not designed for ease of repair, having components which are not readily disassembled. Consequently, expensive instruments and materials must be discarded, even if only a small part of the instrument is worn or defective.

These problems, and a corresponding fear of inadequate decontamination and sterilization, has lead to the wide spread use of disposable instruments, particularly for laparoscopic and other minimal invasive procedures. While these disposable instruments are presumably in operative condition and completely sterile, their use has created new problems. First, disposing of the used instruments, which can be accompanied by hazardous contaminated waste, must be done in an environmentally responsible manner. Further, the use of disposable instruments has substantially added to the cost of providing these surgical procedures in a hospital environment.

What is needed, then, is a system for maintaining an adequate but not excessive inventory of surgical instruments, for repair, sterilization, and recycling of reusable surgical instruments, and a system which will result in lower cost to the hospital and hopefully to the consumer of medical services. Such a system is presently lacking in the prior art.

SUMMARY OF THE INVENTION

The surgical instrument recycling and tracking system of the present invention combines the methods and concepts of just-in-time inventory control with a computerized data entry and tracking system and with reusable surgical instruments adapted for quick disassembly and repair.

A facility for sterilization and maintenance of surgical instruments is remotely located so that it can service a plurality of hospitals, out-patient surgery centers, and similar medical facilities. The sterilization and maintenance facility includes stations for decontamination of used instruments, inspection of decontaminated instruments, repair of instruments which fail inspection including replacement of recyclable and separable components of such instruments, a sterilization station, and a shipping and receiving unit for shipping of sterilized assembled instrument kits and for receiving used instruments from the remote medical facilities.

Also located at the sterilization and maintenance site is a host computer which manages and tracks the flow of information pertaining to the surgical instrument kits within the system, including information entered at a remote data terminal at the shipping and receiving unit at the sterilization and maintenance site.

At each hospital is located at least two remote data terminals, one in the surgical suite and one at the shipping and receiving unit of the hospital. Attached to each of these data terminals are bar code readers by which data identifying and tracking instrument kits are automatically entered into the system. The data terminals at the hospital site electronically link to the host computer at the sterilization and maintenance site through a communications terminal, either wireless or land-line.

Orders for surgical instrument kits needed for surgical procedures scheduled during the next surgical scheduling period at a particular hospital are entered at the data terminal located in the surgical suite. This information is received by the host computer at the sterilization and maintenance site which then communicates with the shipping and receiving department at that same site. Accordingly, selection of the appropriate surgical kit for that procedure is made from the inventory of such kits at the sterilization and maintenance site. It is then identified with a bar code label and placed in the custody of a shipping carrier, such as an overnight delivery service. The shipping carrier, in turn, automatically tracks the instrument kit being delivered by use of its own remote data terminal and bar code reader device. The shipping carrier delivers the ordered surgical instrument kit to the appropriate hospital where it is received and re-acknowledged into the system by the terminal located in the hospital shipping and receiving department. The instrument kit then received is delivered to the instrument holding area of the surgical suite.

Accordingly, it is an object of the present invention to provide a system whereby instruments and other equipment used in surgical procedures can be recycled to their like-new condition so that surgical personnel are assured of proper operation and sterilization of the devices, without having to resort to the expense of an environmentally unsound practice of using and disposing of single-use devices.

It is another object of the system of the present invention to minimize the expense and space which a hospital facility must dedicate to the inventorying and maintenance of reusable surgical instruments and related equipment.

It is a further object of the system of the present invention to provide for high quality reusable surgical instruments for use in surgical procedures while lowering the ultimate cost to the medical facility and to the consumer associated with those instruments.

DESCRIPTION OF THE PREFERRED EMBODIMENT

Figure 1:
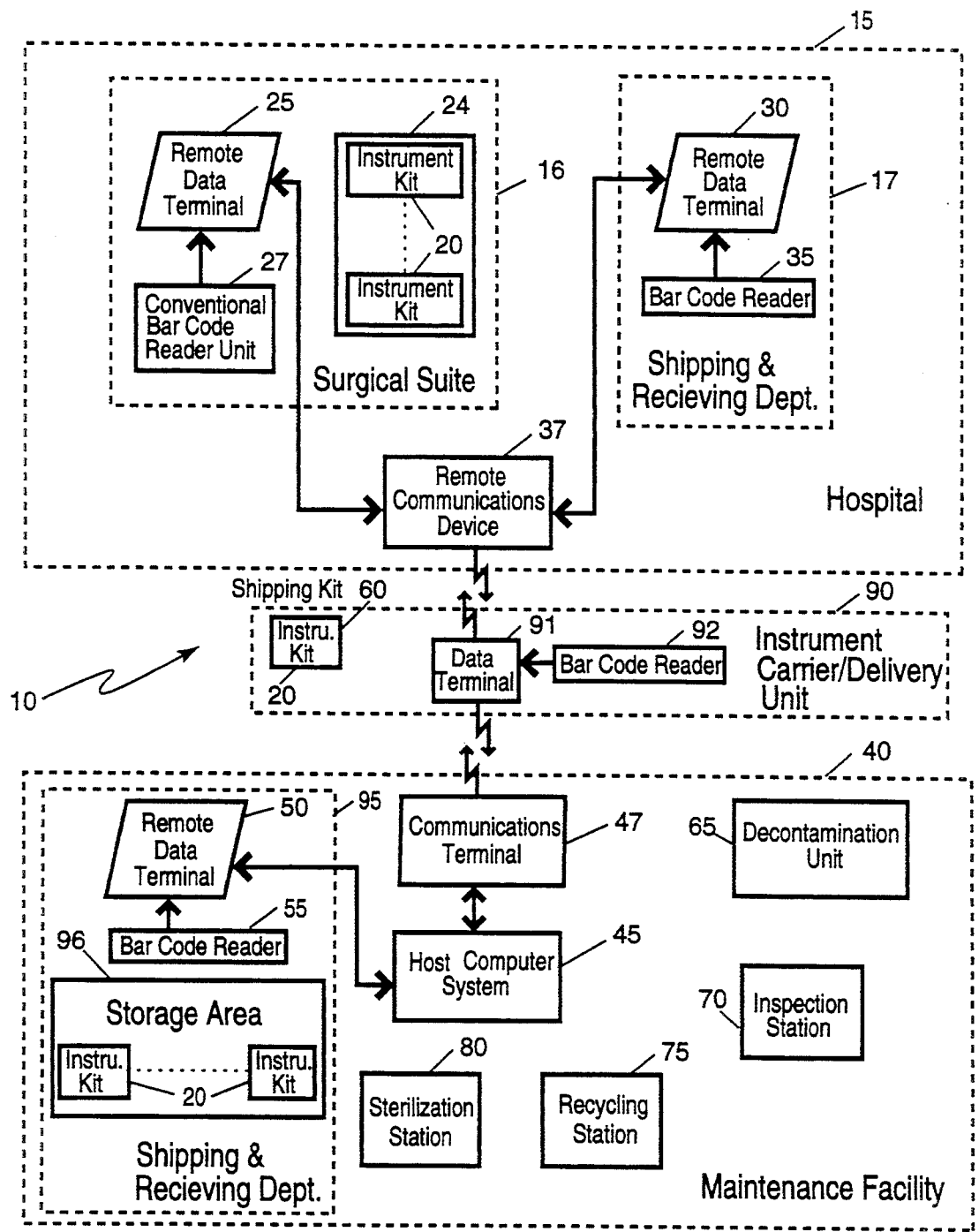
FIG. 1 is a block diagram representation of the system of the present invention.

Referring now to FIG. 1, the surgical instrument recycling and tracking system 10 of the present invention is shown as physically located at or associated with three discrete facilities, a hospital 15, a remote surgical instrument sterilization and maintenance facility 40, and an instrument delivery/carrier unit 90. It will be appreciated by those skilled in the art that hospital 15 can be an existing hospital, a free-standing out-patient surgery center, or other medical facility where surgical instruments are routinely required. The components of system 10 are located preferably in two discrete locations within hospital 15. Conventional surgical suite 16, in which the operating rooms are located, will typically also include a surgical scheduling area (not shown) and an instrument storage area 24. For purposes of implementing the present invention, surgical suite 16 will also include a remote data entry and display terminal 25 of conventional design, and adapted for keyboard entry of data related to surgical procedures and surgical instrument inventory and location tracking, as well as for automatic input of similar data from conventional bar code reader unit 27.

As compared to a prior art instrument tracking system, in hospital 15 the space allocated to instrument storage area 24 will be reduced such that only space needed to temporarily store those instrument kits 20 needed for surgery scheduled during the next scheduling period. It is known by those in the medical field that all instruments normally used in a specific surgical procedure are preferably packed together in such kits.

Hospital shipping and receiving department 17 also includes a remote data terminal 30 and bar code reader unit 35 similar to that located in surgical suite 16. Remote terminal 30 and bar code reader 35 are also used for entry and display of surgical instrument inventory and tracking data used in system 10. Also located in hospital facility 15 is remote communications device 37 by which remote data terminals 30 and 25 are linked to corresponding communication facilities located at sterilization and maintenance site 40 and instrument carrier unit 90.

As can be seen, the majority of the recycling and tracking operations of system 10 are performed within sterilization and maintenance facility 40. Sterilization and maintenance facility 40 includes a shipping and receiving unit 95 by which surgical instrument kits 20 which may be needed by hospital 15 are inventoried in storage area 96. Also located in the shipping and receiving unit 95 are remote data terminal 50 and bar code reader 55 which communicates to host computer system 45. Data is also sent to and received by host computer 45 through communications terminal 47 which is linked, either by wireless communications or conventional land data line, to hospital 15 and instrument carrier 90.

Surgical instruments that have been used by hospital 15 are also received by shipping and receiving unit 95 of sterilization and maintenance facility 40 where they are then delivered to decontamination unit 65. In decontamination unit 65, the contents of a used surgical instrument kit 20 are, in a conventional manner, flushed with hot water and detergent while being agitated with ultrasound in order to loosen any encrustation on the instruments. The instruments in kit 20 are then dried and moved to inspection station 70. In inspection station 70, the instruments are visually inspected and tested to insure that, upon sterilization, they will be meet the performance and quality requirements demanded by hospital 15. Those instruments which do not pass inspection are then taken to repair and recycling station 75. In repair and recycling station 75, the instruments are disassembled and then reassembled using either new replacement parts or parts which have been salvaged from other instruments already within the system. The newly assembled instruments are then retested.

Following reassembly and retesting of the instruments in instrument kit 20, the kit is repacked in conventional manner and sterilized in sterilization station 80. Then it is returned to shipping and receiving unit 95 where it is placed in a protective shipping kit 60 and labeled with a conventional bar code label containing data identifying the kit by reference to standard medical procedure terminology, date and time information, hospital identifier, and the like. It is then placed in temporary storage area 96 until needed by hospital 15.

The physical transportation link between sterilization and maintenance facility 40 and hospital 15 is provided by instrument carrier unit 90 which, in the preferred embodiment, can be a standard common or private carrier. Preferably, carrier unit 90 will include a remote data terminal 91 which is operatively connected to a bar code reader 92. Accordingly, instrument kits 20 which are placed for shipment on carrier unit 90 can be tracked using the bar code label on shipping kit 60 and bar code reader 92. Also, if desired, data identifying the kit and the location and anticipated time of delivery of instrument kit 20 can be communicated by conventional wireless means from remote data terminal 91 to hospital 15 through communications terminal 37 and/or to sterilization and maintenance site 40 through communications terminal 47.

Figure 2:
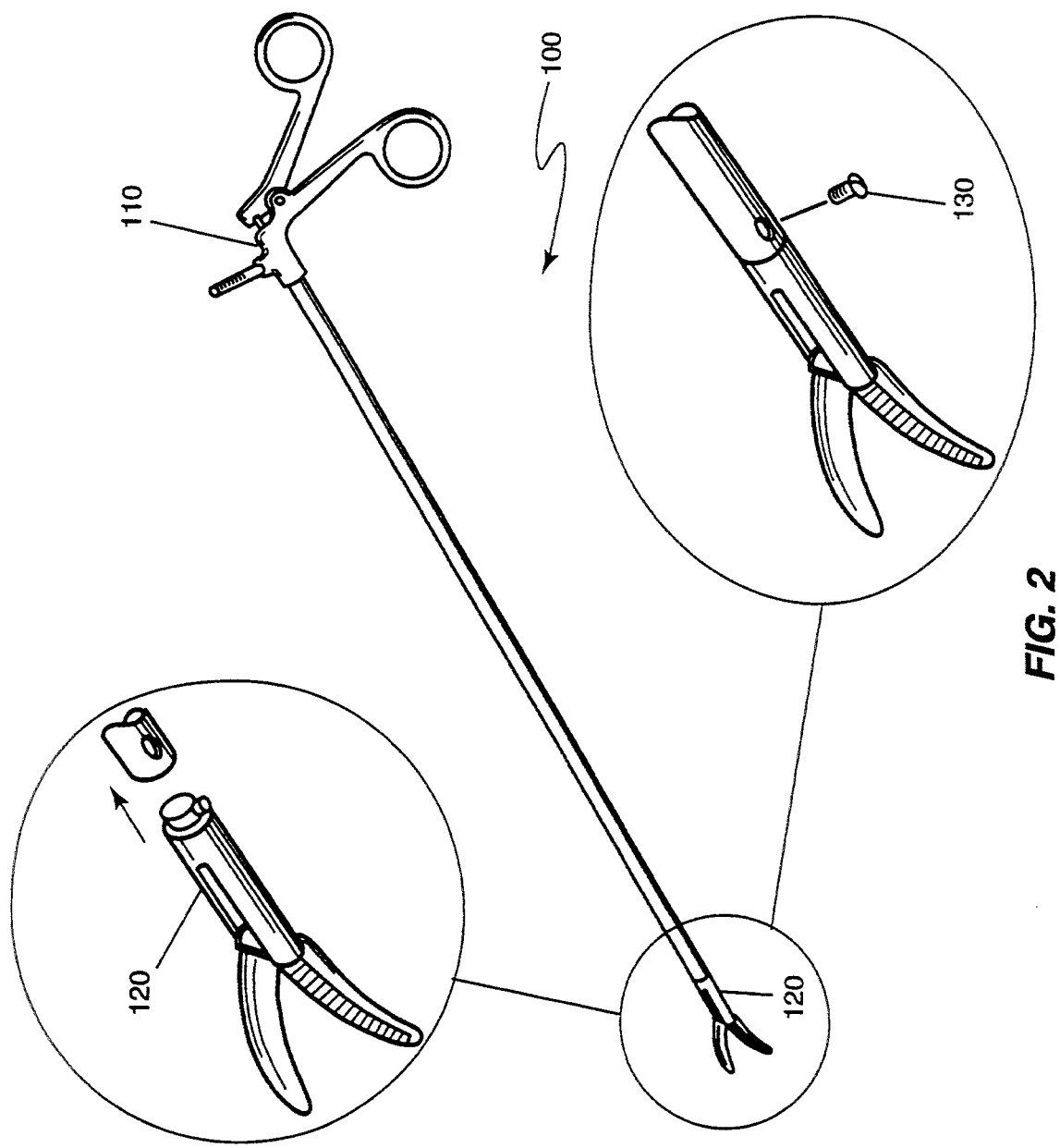
FIG. 2 is a side and partially enlarged view of a surgical instrument of the type to be used in the present invention, in this case grasping forceps for use in minimal invasive surgery.

Looking now at FIG. 2, a typical surgical instrument 100, in this case grasping forceps, is shown. In the preferred embodiment, instrument 100 will include handle 110 and grasping jaws 120, joined by removable screw 130. By using instruments of the type shown in FIG. 2 in the instrument kit 20, the long term cost to hospital 15 can be reduced because of the ability to repair defective instruments using recycled components. For example, if jaws 120 were to become worn or damaged during use, they can be removed and used handle 110 combined with a new jaws 120, and instrument 100 placed back in service. Presently, the entire instrument might be discarded in such instance.

Having identified the components of the system of the present invention, its operation in the preferred embodiment can be described. The scheduling department of surgical suite 16 will electronically link to host computer 45 of remote sterilization and maintenance facility 40 through remote data terminal 25 and modem/wireless communication terminals 37 and 47. Across this communications link, data identifying the needs of such surgical suite 16 (during the next 24 hour scheduling period for example) for particular surgical instrument kits 20 is entered at data terminal 25. Included in this data will be information about the scheduled surgery time and date, the surgical procedure, the location of the procedure, and any needed variations from a standard instrument kit 20 required by the corresponding surgical team. The order for surgical instrument kit 20 and related data is then acknowledged across the communications link by host computer 45. Included in the acknowledgement will be a tracking code (identifying, for example, that particular instrument kit 20 to a specific hospital 15 and procedure) which is transmitted to data terminal 50 in the shipping and receiving unit 25 of sterilization and maintenance facility 40. Accordingly, personnel in the shipping and receiving unit 95 will attach a standard bar code label with such tracking code to an instrument kit 20, or to its protective shipping kit 60, currently in inventory in storage location 96.

Personnel in shipping and receiving unit 95 will then contact instrument carrier 90 which will come to sterilization and maintenance facility 40, pick up one or more instrument kits 20, now preferably packaged in a protective and bar code labeled shipping kit 60, for delivery to the appropriate hospital 15. Transfer of the requested instrument kit 20 from sterilization and maintenance facility 40 to shipping carrier unit 90 is confirmed and tracked by use of bar code reader 92 and data terminal 91. Upon arrival of shipping carrier unit 90 at hospital 15, shipping and receiving unit 17 acknowledges and tracks receipt of the requested surgical instrument kit 20 by means of bar code reader 92 and data terminal 30. Instrument kit 20 is then removed from shipping kit 60 where it is then delivered to temporary storage unit 24 in surgical suite 16. It is then ready for use at the time that the corresponding surgical procedure is scheduled.

Carrier unit 90 can also be used for transfer of used instrument kits 20 from hospital 15 to sterilization and maintenance facility 40. Upon receipt at sterilization and maintenance facility 40, instrument kit 20 is decontaminated as described above in decontamination unit 65. It is then inspected in inspection station 70, repaired or recycled as appropriate in repair and recycling station 75, and then sterilized as a kit in sterilization station 80. Instrument kit 20 is then returned to shipping and receiving unit 95 of sterilization and maintenance facility 40 where it is stored in storage unit 96 awaiting shipment to another hospital 15.

The system 10 as described and claimed can be used to service a plurality of hospitals 15, from a single sterilization and maintenance facility 40, resulting in even greater efficiencies.

Thus, although there have been described particular embodiments of the present invention of a new and useful surgical instrument recycling and tracking system, it is not intended that such references be construed as limitations upon the scope of this invention except as set forth in the following claims.

What I claim is:

1. A system for tracking and recycling of surgical instruments used in a hospital comprising:
    a. a facility for maintenance of said instruments, said maintenance facility remotely located from said hospital;
    b. means, located at said maintenance facility, for decontamination, inspection, and sterilization of said instruments after use at said hospital;
    c. means for transporting kits comprised of said sterilized instruments from said maintenance facility to said hospital and for transporting used surgical instruments from said hospital to said maintenance facility;
    d. host computer means for receiving, tracking, processing, and transmitting data associated with said instrument kits; and
    e. at least one remote data terminal located at said hospital and electronically linked to said host computer means, said data terminal adapted for entry of data associated with said instrument kits, said data including orders for said kits needed for surgical procedures scheduled at said hospital.

2. The system of claim 1 where said surgical instruments comprise components separable and replaceable by use of hand tools.

3. The system of claim 1 further comprising at least one data terminal located at said maintenance facility and electronically linked to said host computer, said terminal adapted for entry and receipt of data associated with said instrument kits.

4. The system of claim 3 further comprising bar code labels attached to and identifying said instrument kits and means located at said hospital and said maintenance facility, and electronically linked to said host computer, for reading data on said bar code labels.

5. The system of claim 4, said instrument kit transport means further comprising means for reading and recording data on said bar code labels.

6. The system of claim 5 further comprising means on said transport means for electronically transmitting said recorded bar code data to said hospital.

7. A method of tracking surgical instruments used in hospitals comprising the steps of:
    a. communicating from a data terminal at said hospital to a host computer data identifying surgical procedures scheduled to be performed at said hospital during a scheduling period;
    b. combining at an instrument maintenance facility separate from said hospital a group of said cleaned and sterilized instruments into instrument kits, each of said kits corresponding to one of said surgical procedures;
    c. transporting by carrier from said maintenance facility to said hospital said instrument kits corresponding to said scheduled surgical procedure data communicated from said hospital to said host computer;
    d. transporting by carrier from said hospital to said maintenance facility said instrument kits after use at said hospital; and
    e. cleaning and sterilizing at said maintenance facility said instruments from said instrument kits.

* * * * *